United States Patent [19]

McConnell

[11] Patent Number: 4,865,484

[45] Date of Patent: Sep. 12, 1989

[54] SINGLE RELEASE, MULTIPLE AXIS COUPLING

[76] Inventor: Thomas E. McConnell, Rte. 2, Box 89, Greenville, Tex. 75401

[21] Appl. No.: 80,483

[22] Filed: Jul. 31, 1987

[51] Int. Cl.[4] .............................................. F16B 7/04
[52] U.S. Cl. ..................................... 403/59; 403/391; 403/400; 248/286
[58] Field of Search .................. 403/59, 55, 391, 369, 403/396, 400, 385, 346, 373, 395, 394; 248/286, 287, DIG. 4, 296

[56] References Cited

U.S. PATENT DOCUMENTS

| | | | |
|---|---|---|---|
| 551,358 | 12/1895 | Benecke | 403/389 |
| 1,408,834 | 3/1922 | Seavey | 403/59 |
| 1,604,870 | 10/1926 | AsMan | 403/396 |
| 2,310,276 | 2/1943 | Bilz | 403/385 |
| 2,532,173 | 11/1950 | Lewis | 248/286 X |
| 2,696,996 | 12/1954 | Engelhardt | 403/391 |
| 3,097,037 | 7/1963 | Gainer et al. | 403/400 X |
| 3,810,462 | 5/1974 | Szpur | |
| 4,050,661 | 9/1977 | Wooldridge | 248/296 X |
| 4,217,061 | 8/1980 | Eiland et al. | |
| 4,576,501 | 3/1986 | McConnell | 403/59 |
| 4,708,510 | 11/1987 | McConnell et al. | |
| 4,796,846 | 1/1989 | Meier et al. | 403/59 X |

FOREIGN PATENT DOCUMENTS 125512 of 1919 United Kingdom ................ 403/391

*Primary Examiner*—Peter M. Cuomo
*Attorney, Agent, or Firm*—Dennis T. Griggs

[57] ABSTRACT

A single release, multiple axis coupling device for securing and positioning patient support equipment during orthopedic surgery. The coupling device can be released from or securely locked into a rigid position by a single rotation of an actuator shaft. The released or locked configuration is achieved by a rotational movement of the actuator shaft and a reciprocal axial movement of a cylindrical piston assembly. By displacing the cylindrical piston assembly within a housing chamber, either two or three movable coupling members can be rigidly secured to or released from the support shaft upon which the coupling assembly is mounted.

1 Claim, 5 Drawing Sheets

SINGLE RELEASE, MULTIPLE AXIS COUPLING

FIELD OF THE INVENTION

The present invention relates generally to clamping devices, and in particular to an articulated coupling clamp having multiple axes of rotation.

BACKGROUND OF THE INVENTION

During orthopedic surgery, various portions of a patient's body are elevated above an operating table. To accommodate and sustain the elevated position, patient support devices are routinely used, including slings, straps and angular support equipment. Conventional support equipment is difficult to adjust or reposition. Each adjustment requires a disconnection and recoupling of the accompanying support apparatus. During surgery, this repositioning procedure is not only cumbersome, but is also time consuming. Ideally, such patient support equipment should be released and secured by a single actuator.

DESCRIPTION OF THE PRIOR ART

Conventional clamps having two or more axes of rotational adjustment are also provided with separate release/lock actuators for controlling the orientation of a single support device. Operation of the separate actuator must be carefully coordinated to reposition the elevated body member during operation. Accordingly, there is a need for a single release, multiple axis coupling patient support which can be quickly, easily and securely adjustable upward, downward or at various angles about a vertical support shaft.

OBJECTS OF THE INVENTION

The principal object of the present invention is to provide an improved coupling device having multiple positioning movements to accommodate a wide range of angles about a vertical support shaft.

A related object of the invention is to provide an improved coupling device and support assembly which is operative below and in an offset position relative to the patient's supported body member.

Another object of the invention is to provide a multiple axis coupling device which can be locked into a rigid position or released by a single release actuator.

SUMMARY OF THE INVENTION

The present invention provides a coupling assembly allowing for movement and positional control of various portions of a patient's body. Typically, an ankle and lower leg are supported and movable by a support rod having either two or three axes of rotation about a vertical support shaft.

In a double axis configuration, the single rod is horizontally rotatable about the vertical support shaft axis, while also vertically rotatable about a piston through which the vertical support shaft is extended. Double axis rotational movement is permitted by axial movement of a single cylindrical piston into the coupling device's housing chamber. Such piston movement is provided in response to a counterclockwise rotation of a single actuator shaft. Alternatively, movement can be "frozen" or prohibited by a clockwise rotation of the actuator shaft and subsequent withdrawal of the cylindrical piston from the coupling device's housing chamber. By engaging various portions of the coupling assembly, the coupling device is locked in a rigid position relative to the vertical support shaft.

In a triple axis configuration, not only is the support rod both vertically and horizontally rotatable (double axis), but the support rod is also capable of being rotated about its own axis. Movement about the three rotational axes is permitted by a counterclockwise rotation of a single actuator shaft and reciprocating withdrawal of a double piston assembly from the coupling device's housing chamber. By using two pistons instead of one, the third axis of rotation is permitted. However, when the single actuator shaft is tensioned in a clockwise manner, both pistons are simultaneously engaged with various portions of the coupling assembly and the entire device is locked in a rigid position relative to the vertical support shaft.

The coupling assembly, whether it be double or triple axis of movement, is attached below and in offset relation to the patient's supported body member. This type of supporting arrangement provides the physician with an open working area above the patient's supported member during the performance of a surgical procedure. Also, whether the physician requires either the two or the three degrees of coupling freedom, the locking and release action of the coupling assembly is easily and quickly obtained by a single rotational movement of a threaded actuator shaft.

DETAILED DESCRIPTION OF THE PREFERRED EMBODIMENT

Figure 1:
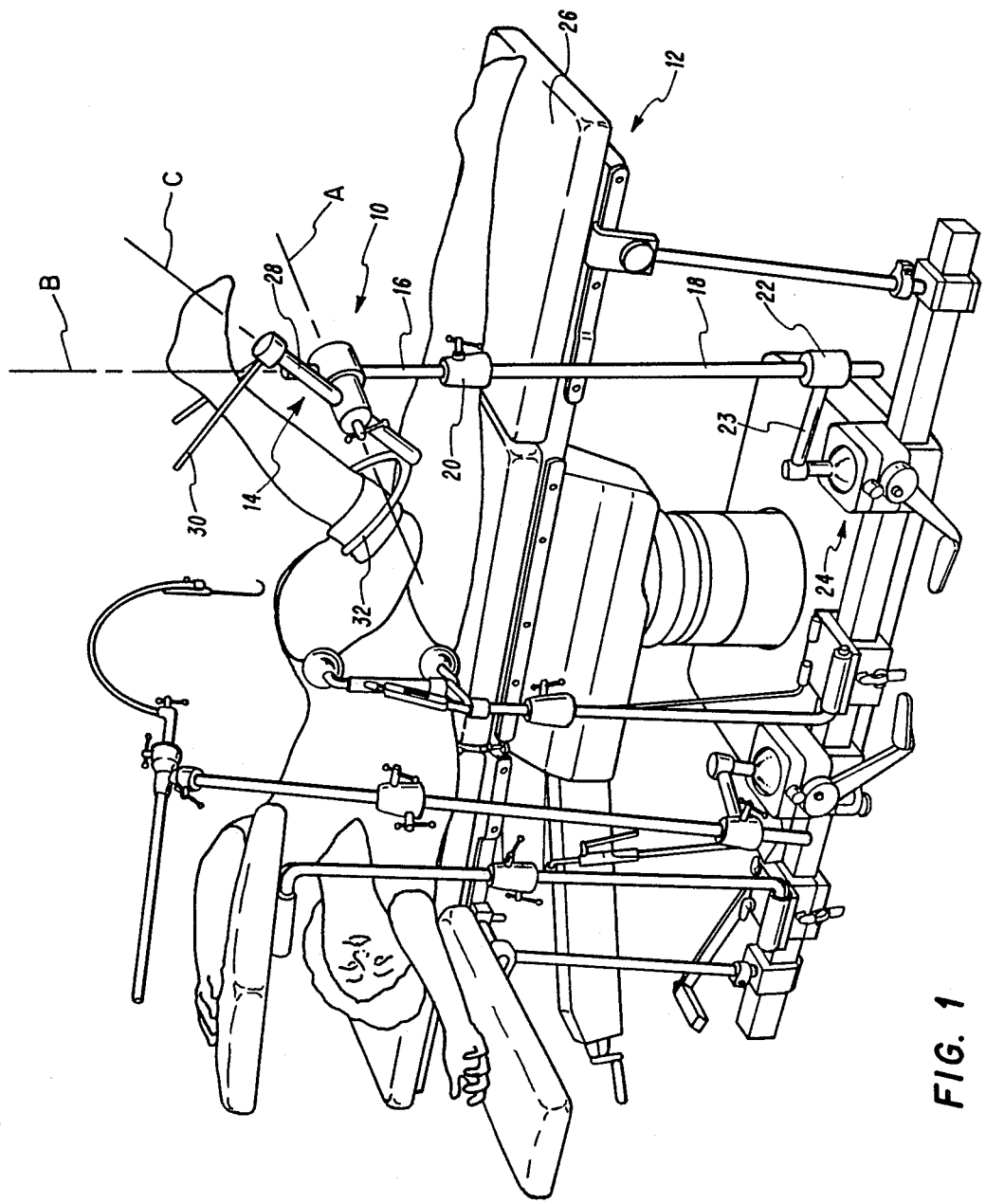
FIG. 1 is a perspective view of the single release, multiple axis coupling device illustrating its operating configuration, functionally connected to an operating table and supporting a patient's ankle and lower leg.

In the description which follows, like parts are indicated throughout the specification and drawings with the same reference numerals, respectively. The drawings are not necessarily to scale and certain parts have been exaggerated to better illustrate details of the present invention.

Referring now to FIG. 1, a single release, multiple axis coupling assembly is indicated generally by reference number 10. As illustrated in FIG. 1, the single release, multiple axis coupling assembly 10 is shown functionally interposed between an operating table 12 and an ankle and lower leg retaining assembly 14. The coupling assembly is fastened to a support shaft 16, whereby the support shaft is telescopically extendable from a tubular section 18. The support shaft 16 extends as a sleeve within the tubular section 18, and is fastened at a desired height by clamp 20. The tubular section 18 is connected to a secondary clamp 22 which is connected by an offset arm 23 to a horizontally movable clamp assembly 24. It will be appreciated that the lower leg retaining assembly 14 is attached below the patient support pad 26 so that the patient's leg is held in an open position accessible to the physician.

The ankle and lower leg assembly 14 is securely held in an upright position offset from the patient's upper exposed hip area. The entire ankle and lower leg assembly 14 can be raised or lowered by a corresponding extension or retraction on the support shaft 16 within the tubular section 18. Once the ankle and lower leg are elevated at a proper position, further "fine tuning" adjustments of the patient's ankle and lower leg are made by the single release, multiple axis coupling assembly 10.

Adjustable within the coupling assembly 10 is a support rod 28. The support rod 28, ankle retainer 30, and leg retainer 32 comprise the ankle and lower leg retaining assembly 14. The ankle retainer 30 is a V-shaped member securely attached to one end of the support rod 28. The leg retainer 32 is a U-shaped member attached to the opposite end of the support rod 28. The ankle and leg retainer members 30, 32 firmly support the patient's lower leg and ankle, whereby the patient's hip is maintained in a relaxed but stable position conducive for surgery.

Figure 2:
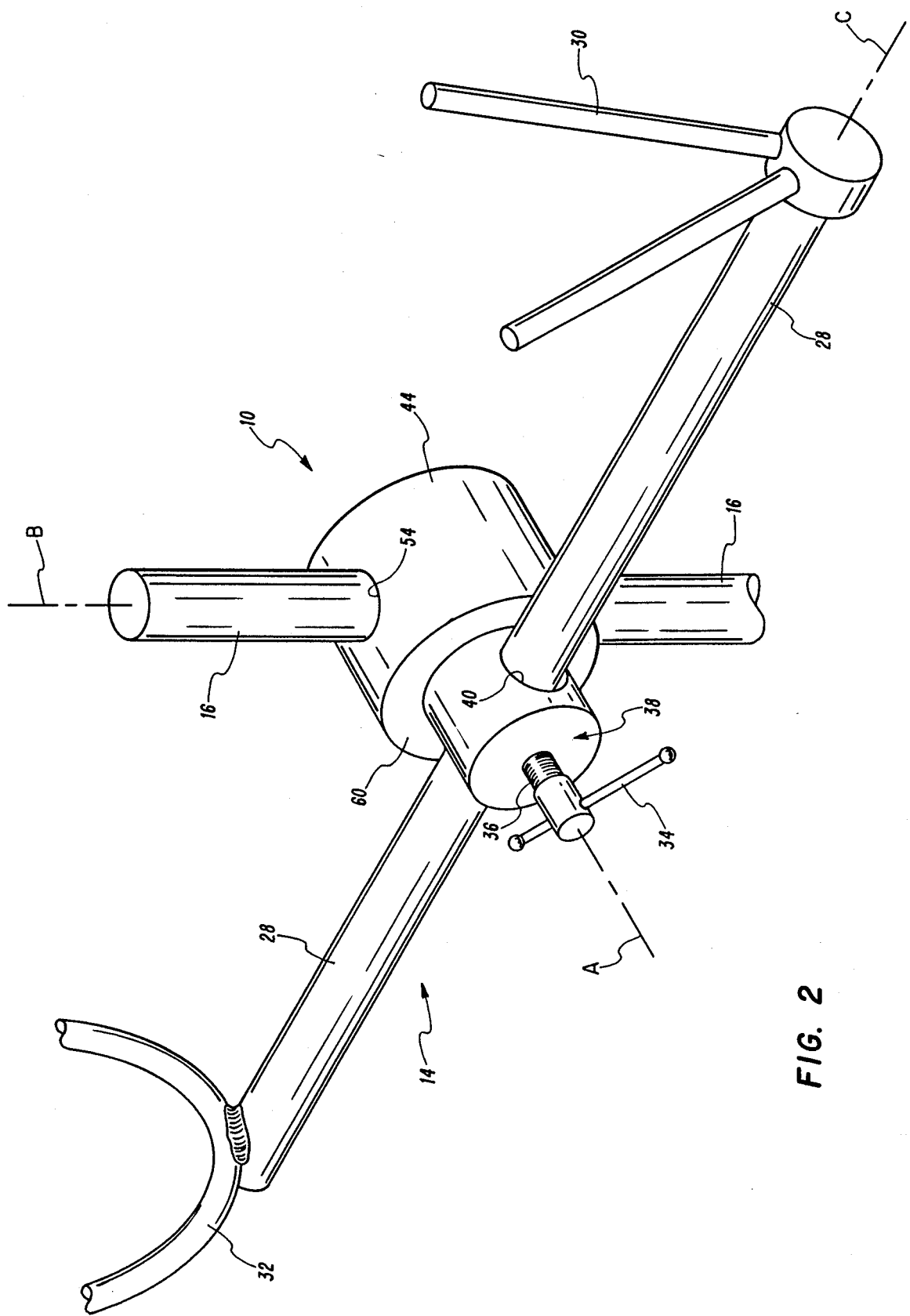
FIG. 2 is a perspective view, partially cut away, of the single release, triple axis coupling assembly of FIG. 1.
Figure 3:
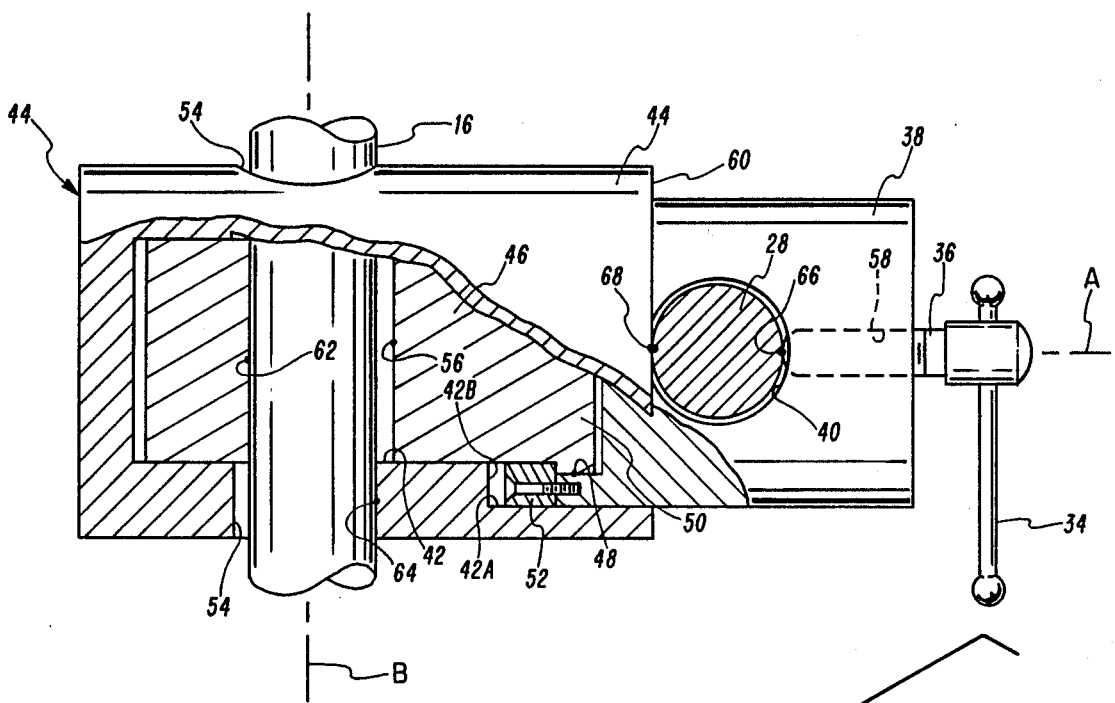
FIG. 3 is a side elevational view, partly in section, of the single release, triple axis coupling device.
Figure 4:
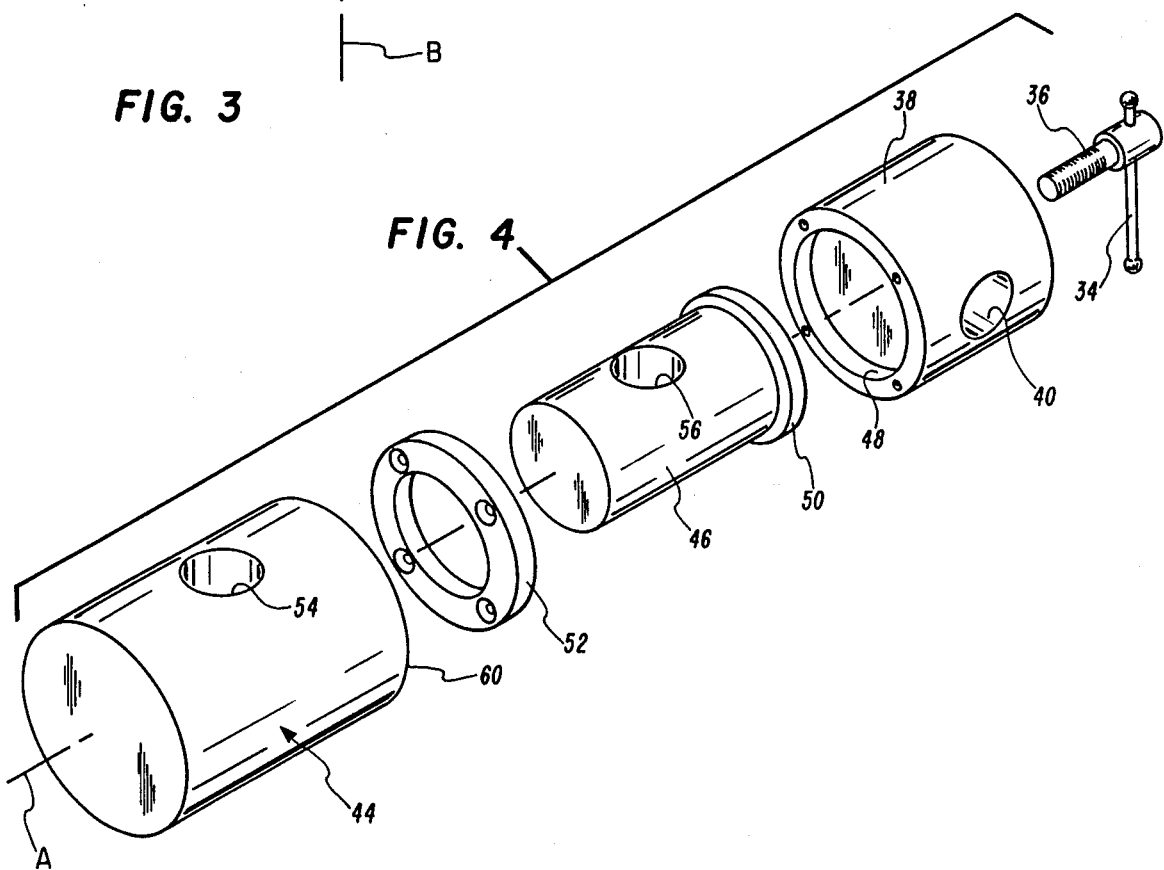
FIG. 4 is an exploded perspective view of the single release, triple axis coupling assembly.

The single release, multiple axis coupling assembly 10 as shown in FIGS. 2, 3, and 4 has three axes of rotation A, B and C. A single counterclockwise movement of the handle 34 will retract a threaded actuator shaft 36 from a piston 38. The actuator shaft, when retracted, will simultaneously release the support rod 28, piston 38, and coupling assembly housing 44, from their secured (engaged) positions. The released support rod 28 is now free to move within bore 40 of piston 38, as is piston 38 free to rotate within a first coupling or housing chamber 42 of the housing 44, and finally, the housing 44 is now free to move vertically on and horizontally about the vertical support shaft 16. Rotational movement of the piston 38, as well as rotational and lateral movement of the support rod 28 and housing 44, make possible a wide variety of lower leg adjustment positions. Once a desired position is reached, a clockwise movement of the handle 34 and attached actuator shaft 36 will securely engage all members of the coupling assembly 10.

The multiple positioning movements of a triple axis coupling assembly 10 is made possible by lateral movements of the piston 38 and its piston head portion or tandem piston 46. Piston 38 is cylindrical having an end portion with a threaded passage or bore 58 (to accommodate the threaded actuator shaft 36) and a second coupling chamber or pocket 48 at opposite ends of the cylindrical piston 38, respectively. Piston 46 is also of cylindrical shape having a flange 50 at one end of the cylinder. The flange 50 is completely recessed within the pocket 48 of piston 38 and is secured to piston 38 by an end cap 52. The end cap 52 has an inside diameter larger than the diameter of the piston 46, but smaller than the diameter of flange 50. Therefore, when the end cap 52 is secured to the end of piston 38, the recessed flange 50 and connected piston 46 cannot be laterally separated from piston 38. The end cap 52 and accompanying piston 46 are slideably received within a counterbore 42A formed in housing 44, and a gap remains between the end cap 52 and housing shoulder 42B, whereby piston 38 is rotatable about its own axis A when disengaged.

As shown in FIG. 3, piston 46 and part of piston 38 are completely recessed within the housing chamber 42. Piston 46 is aligned whereby the support shaft 16 is placed within a bore 56 passing through piston 46 and the housing bore 54. The housing bore 54 and piston bore 56 are of slightly larger diameter than the support shaft, so that when disengaged, the housing 44 and piston 46 are independently movable relative to the support shaft 16.

The bore 40 passing completely through piston 38 accommodates the support rod 28. The support rod 28 is placed within the slightly larger piston bore 40, and the piston 38 is movable relative to support rod 28 when disengaged. As illustrated in FIGS. 2 and 3, the threaded actuator shaft 36 is placed within the threaded bore 58 extending axially through the end portion of piston 38 to the side of support rod 28 disposed in piston bore 40. A clockwise movement of the handle 34 will extend the actuator shaft 36 against the support rod 28. Extension of the actuator shaft will compress the support rod 28 against the annular end face 60 of the housing 44. The tandem piston 46 is subsequently drawn through the housing chamber 42 to compress the support shaft 16 along the tandem piston shaft interface 62 and the housing interface 64.

Thus, clockwise rotation of the actuator shaft will simultaneously "freeze" all movable members of the coupling assembly, with the support rod 28 being compressed by the actuator shaft 36 at point 66, and by the housing face 60 along interface 68.

Figure 5:
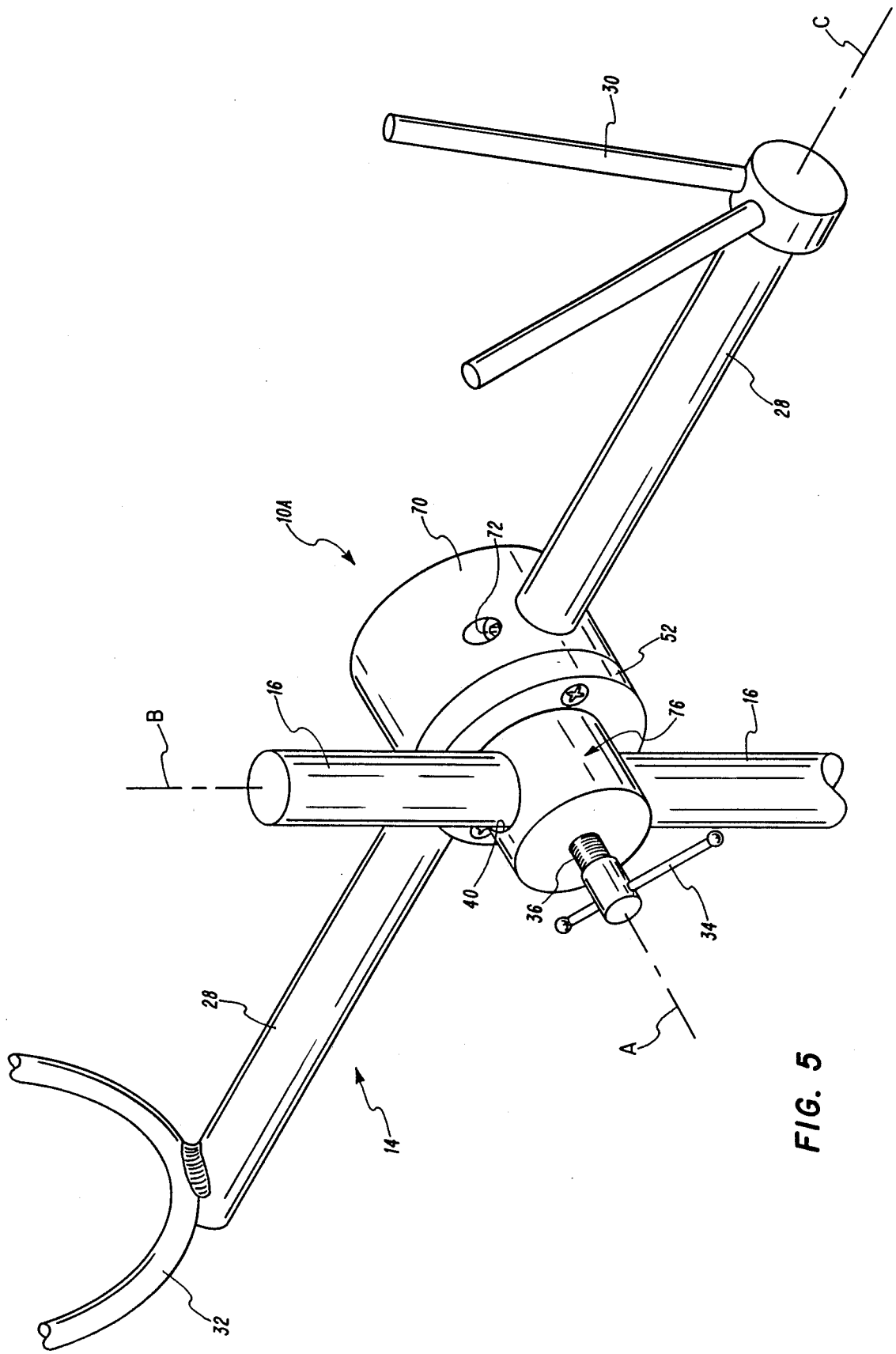
FIG. 5 is a perspective view, partially broken away, of the single 0120 release, double axis coupling assembly.

Referring now to FIG. 5, a single release, multiple axis coupling assembly 10A has only two axes of rotation A, B. The housing 70 is rigidly coupled onto the support rod 28 by a set screw 72. Rod 28 extends through the housing bore 74 and is seized by set screw 72. Support shaft 16 is received within an enlarged piston bore 40. By preventing support rod movement within the housing bore, the third axis of rotation is eliminated.

Figure 6:
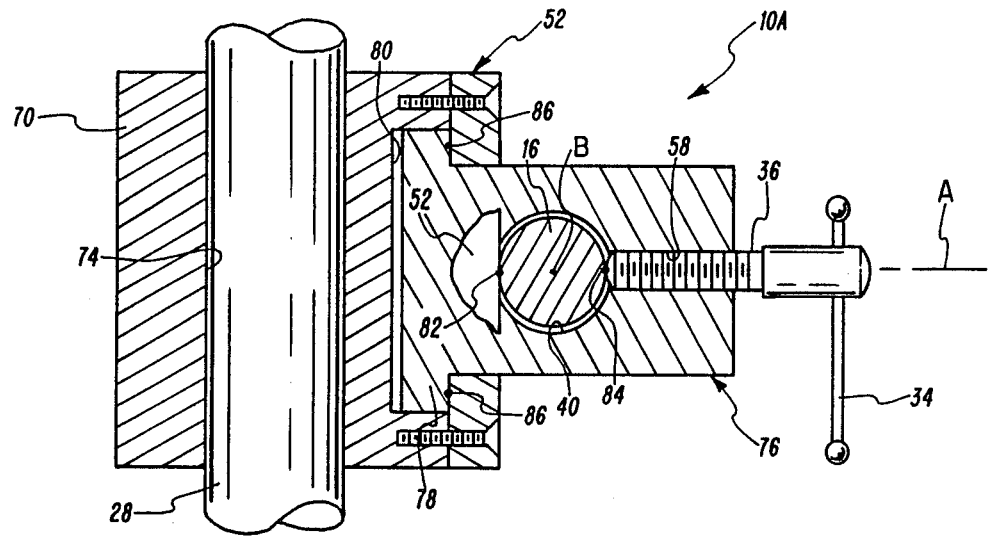
FIG. 6 is a side elevational view, partly in section, of the single release, double axis coupling assembly.
Figure 7:
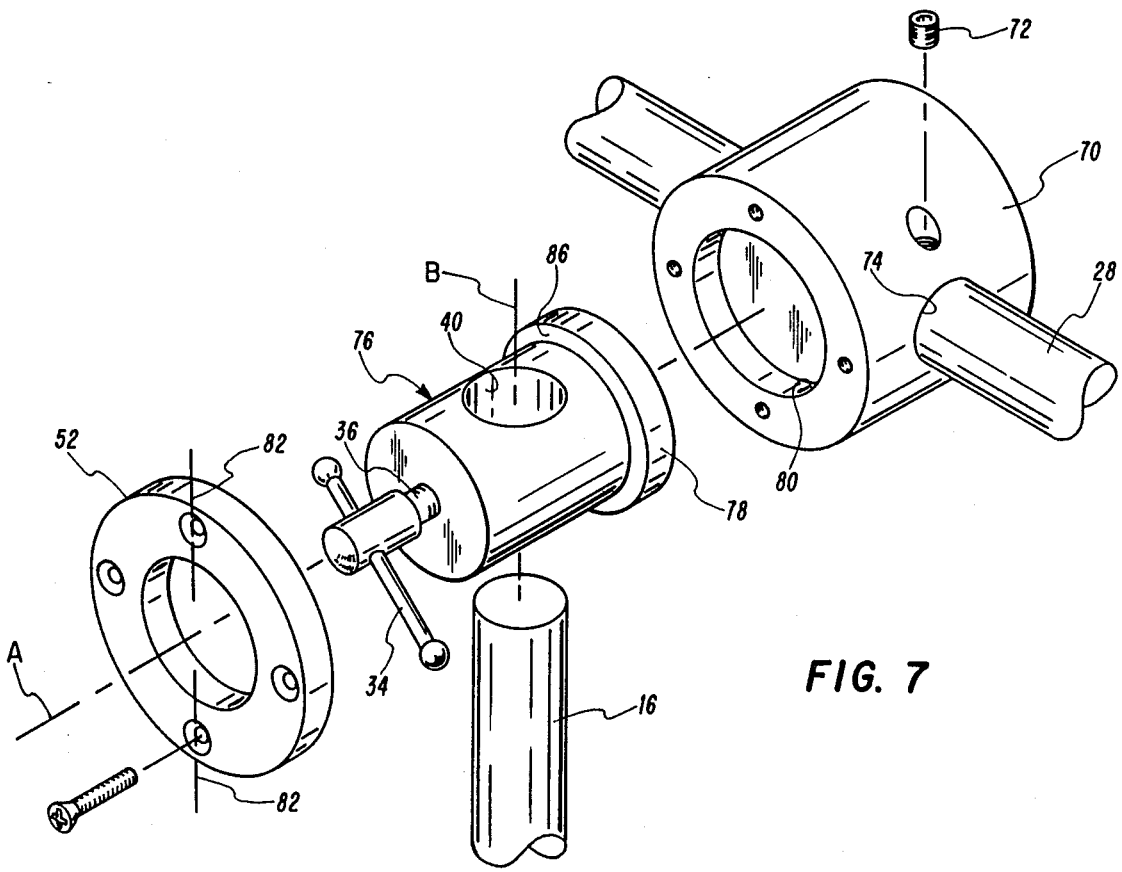
FIG. 7 is an exploded perspective view of the single release, double axis coupling assembly.

Referring now to FIGS. 5, 6 and 7, a movable piston 76 is cylindrical in shape having a flange 78 of larger diameter at one end of the cylinder. The flange 78 is recessed within a housing pocket 80 and retained within the pocket by an end cap 52. The pocket 80 is deeper than the flange, thereby permitting axial movement of the piston 76 from the locked position of FIG. 6 to the released position. When locked, support rod 16 is compressed at interface points 82, 84 and flange 78 is compressed against the end cap 52 at interface 86. In the disengaged or released position, the piston 76 is rotatable within the housing pocket 80 about axis A, and is rotatable around support shaft 16 about axis B.

The single release, double axis coupling assembly 10 is similar to that of the single release, triple axis coupling assembly as described above. The support shaft 16 is placed within a piston bore 40. The cylindrical piston 76 has a flange 78 of slightly larger diameter located at one end of the piston. The flanged portion or end is placed within a housing pocket 80 and confined therein by an end cap 52. In a disengaged position, the piston 76 is rotatable within the housing pocket 80. A threaded actuator shaft 36 is received in a threaded passage 58 which extends from the non-flanged end of the cylindrical piston to the piston bore 40. Rotational movement of the handle 34 will extend the threaded actuator shaft 36 against the support shaft 16 placed within the piston bore 40.

In response to the clockwise turning movement of the actuator shaft 36, the piston 76 is drawn outward in relation to the housing chamber 70. Sufficient clockwise tensioning of the handle 34 will compress the support shaft 16 against the outside annular face along the dotted line 82 which appears on the end cap 52 of FIG. 7. Simultaneously, piston flange 78 is compressed against end cap 52 at 86. Counterclockwise rotation of the handle and subsequent inward movement of the piston 76 will permit rotational and lateral movement of the piston 76 about the support shaft 16, and further permit rotational movement of the piston 76 within the housing pocket 80.

Although the invention has been described with reference to a specific embodiment, the foregoing description is not intended to be construed in a limiting sense. Various modifications to the disclosed embodiment as well as alternative applications of the invention will be suggested to persons skilled in the art by the foregoing specification and illustrations. It is therefore contemplated that the appended claims will cover any such modifications, applications or embodiments as fall within the true scope of the invention.

What is claimed is:

1. A single release, multiple axis coupling assembly comprising, in combination:

a housing having a first bore defining a first coupling chamber and having a second bore extending transverse to said first bore for receiving a first support shaft;

a piston having a head portion received within said first coupling chamber and disposed for axial displacement and rotational movement within said first coupling chamber, said piston having an end portion projecting out of said housing, said piston head portion having a first passage which is alignable with said second bore of said housing for receiving the first support shaft and said piston end portion having a second passage for receiving a second support shaft;

tightening means coupled to said piston end portion for engaging said second support shaft disposed within said second passage of said piston end portion and holding the second support shaft into engagement with said housing while simultaneously drawing said piston into engagement with said first support shaft disposed within said second bore of said housing, whereby the first support shaft is compressed between said piston and said housing, the second support shaft is compressed between said housing and said tightening means, and said housing is compressed between the first and second support shafts in response to actuation of said tightening means;

said piston end portion having a bore defining a second coupling chamber;

said piston head portion having an annular flange movably disposed for rotation within said second coupling chamber of said piston end portion; and, an end cap mounted onto said piston end portion for retaining said annular flange within said second coupling chamber of said piston end portion, said end cap having an opening through which said piston head portion extends.

* * * * *